United States Patent [19]
Sakisako et al.

[11] Patent Number: 4,749,552
[45] Date of Patent: Jun. 7, 1988

[54] AUTOMATIC TITRATION ANALYSIS APPARATUS

[75] Inventors: Hitoshi Sakisako; Masashi Kimura, both of Tokyo, Japan

[73] Assignee: Ebara Densan Ltd., Japan

[21] Appl. No.: 894,308

[22] Filed: Aug. 6, 1986

[51] Int. Cl.$^4$ ............................................. G01N 31/16
[52] U.S. Cl. ...................................... 422/75; 422/62; 436/80; 436/102; 436/163; 436/51
[58] Field of Search ....................... 422/55, 62, 75, 76, 77, 422/80, 102, 105, 231; 436/51, 163, 175

[56] References Cited

U.S. PATENT DOCUMENTS

| | | | |
|---|---|---|---|
| 2,989,377 | 6/1961 | Leisey | 422/77 |
| 3,540,849 | 11/1970 | Neti et al. | 436/175 |
| 3,625,655 | 12/1971 | Culp et al. | 436/51 |
| 3,717,435 | 2/1973 | Ertl et al. | 422/75 |
| 3,759,669 | 9/1973 | Aaron et al. | 422/231 |
| 4,165,218 | 8/1979 | Vanhumbeeck et al. | 436/51 |
| 4,410,550 | 10/1983 | Gaskill | 422/266 |
| 4,425,380 | 1/1984 | Nuzzi et al. | 134/22.16 |
| 4,526,755 | 7/1985 | Vincent et al. | 436/175 |

*Primary Examiner*—Michael S. Marcus
*Attorney, Agent, or Firm*—Steinberg & Raskin

[57] ABSTRACT

Automatic titration analysis apparatus includes a sampling mechanism, a titration mechanism, an analysis mechanism and a control mechanism. The sampling mechanism takes a prescribed quantity of a sample for analysis in accordance with a first signal. The titration mechanism titrates a prescribed quantity of a reagent for analysis of the sample and provides a titer at an end point of the titration according to second signals. The analysis mechanism receives the sample from the sampling mechanism, analyzes the sample and converts a change in the physical properties of the sample caused by the titration into an electrical quantity. The control mechanism provides and applies the first signal to the sampling mechanism, provides and applies the second signals to the titration mechanism, receives the titer from the titration mechanism, receives the electrical quantity from the analysis mechanism, sets the quantity of the sample converted and the titer of the reagent to prescribed values, reads the titer at the end point of the titration, outputs the measured density of the sample calculated therefrom, and controls in sequence the operations of the sampling, titration and analysis mechanisms.

10 Claims, 3 Drawing Sheets

AUTOMATIC TITRATION ANALYSIS APPARATUS

BACKGROUND OF THE INVENTION

The present invention relates to automatic titration analysis apparatus. More particularly, the invention relates to automatic titration analysis apparatus which automatically measures the density of a liquid.

Chemical analysis is indispensable, in general, for operational control of chemical reaction apparatus and treatment apparatus wherein treatment is made with chemicals added as agents for treatment, or for control of the quality of industrial water and industrial waste water, or the like. Chemical analysis has thus far been conducted fairly rapidly by experts in the analytical art and by the use of improved analysis apparatus. Nonetheless, there are still problems that pertinent measurements take some time, human errors are inevitable, and the work load of the analyzers becomes too heavy when repeated continuous analysis is conducted.

For quality control and process control in the production processes of a chemical plant, in particular, it is essential that accurately measured values be obtained constantly, and that these values be fed back to the production processes, so that the development of apparatus for chemical analysis which is free from the aforementioned problems has long been awaited.

The apparatus of the invention may be applied to any known titration analysis method wherein the properties of a sample, that is, the physical or chemical properties thereof including electromagnetic, optical and other properties, are changed by the titration of a reagent. Therefore, the apparatus of the invention may be used very effectively for rationalizing the analytical operations in the operational control of chemical reaction apparatus, the quantity or supply of any chemicals, raw materials or auxiliary materials, the qualities of intermediate or final products in various fields of industry and the quality of industrial water, industrial waste water, etc.

SUMMARY OF THE INVENTION

The principal object of the invention is to provide apparatus which resolves the problems of known apparatus in the art.

An object of the invention is to provide apparatus for rationalizing the analytical operations in the operational control of chemical reaction apparatus, effectively and reliably.

Another object of the invention is to provide apparatus for rationalizing the analytical operations in the operational control of the quantity of supply of any chemicals, raw materials or auxiliary materials effectively and reliably.

Still another object of the invention is to provide apparatus for rationalizing the analytical operations in the operational control of the qualities of intermediate or final products in various fields of industry, effectively and reliably.

Yet another object of the invention is to provide apparatus for rationalizing the analytical operations in the operational control of the quality of industrial water, industrial waste water, etc, effectively and reliably.

Another object of the invention is to provide apparatus which enables an almost unattended, rapid, repeated and continuous attainment of accurately measured values.

Still another object of the invention is to provide apparatus having a feedback control mechanism for controlling a process such as, for example, an etching process and greatly rationalizing the qualities in a sample generating source.

Yet another object of the invention is to provide titration analysis apparatus having a large energy-saving and simplification of the maintenance and control of the sample generating source.

Another object of the invention is to provide titration analysis apparatus for products of improved and stabilized quality.

The automatic titration analysis apparatus of the invention meets the aforedescribed needs and has a sampling mechanism for taking a prescribed quantity of a sample, a mechanism for titrating with a reagent, an analysis mechanism for converting the reception of the sample and the reagent, as well as the physical or chemical change in the sample by the titration of the reagent, into electrical quantities and outputting them, and a control mechanism for providing sequence control of the operations of the sampling, titration and analysis mechanisms while reading the titer of the reagent and outputting the results of the analysis.

BRIEF DESCRIPTION OF THE DRAWINGS

For a fuller understanding of the invention, reference is had to the following description, taken in connection with the accompanying drawing, in which.

DESCRIPTION OF PREFERRED EMBODIMENTS

Figure 1:
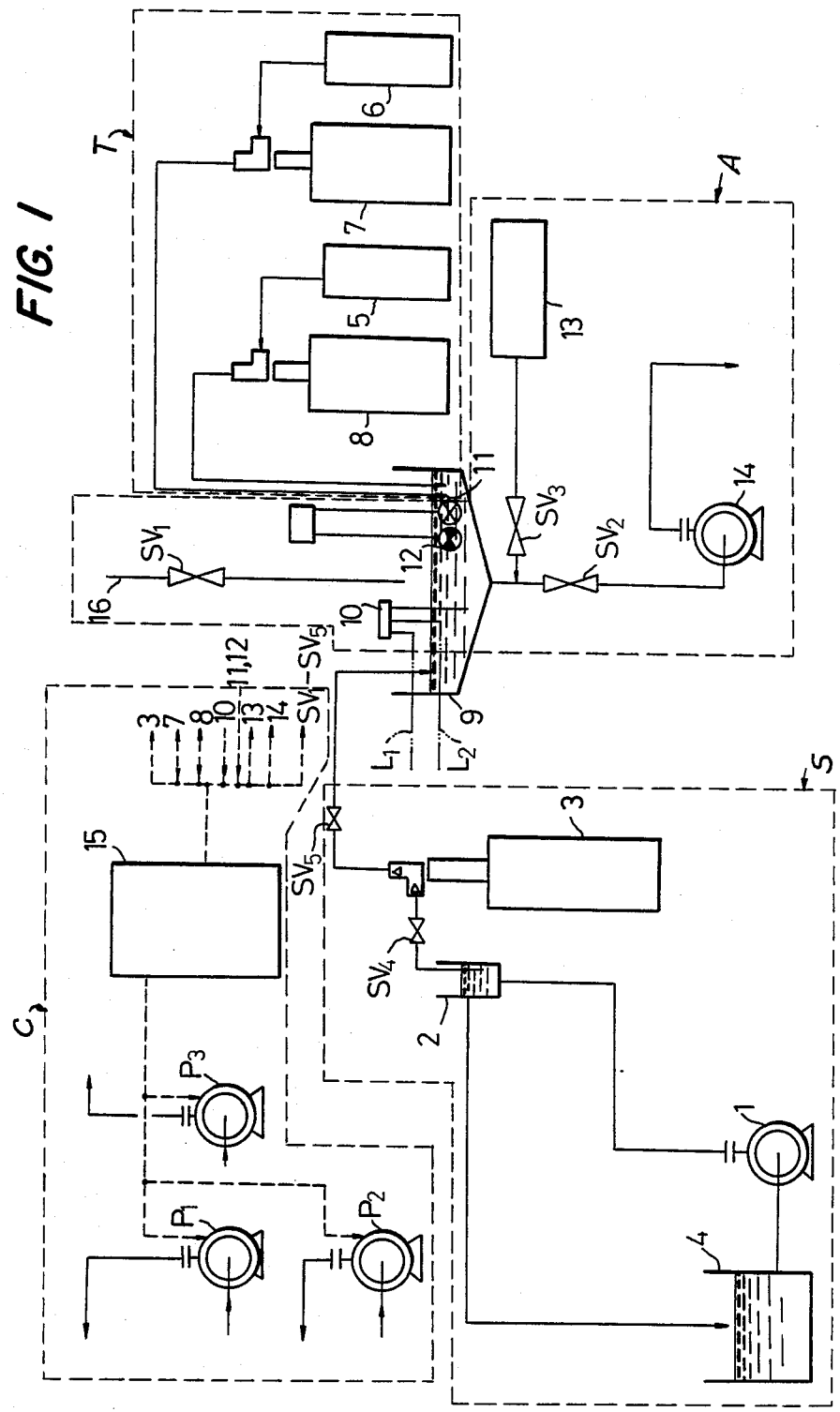
FIG. 1 is a block diagram of an embodiment of the automatic titration analysis apparatus of the invention.

The automatic titration analysis controlling apparatus of the embodiment of FIG. 1 is applied to the control of the density of an etching liquid used for dissolving a specific quantity of copper and removing it from an electric circuit board such as, for example, a printed circuit board. The apparatus of FIG. 1 automatically maintains the respective densities of hydrogen peroxide, sulfuric acid and copper contained in the etching liquid within prescribed ranges. The etching process is thus rationalized to a high degree.

The apparatus of the invention permits not only an automatic titration analysis under the sequence control of the density of the etching liquid, but also a feedback of the results of the analysis to a mechanism regulating the density of the etching liquid. This permits a simple and accurate control of the density of the etching liquid. The automatic titration analysis mechanism of the invention consists primarily of a sampling mechanism S for taking samples, a reagent titration mechanism T, an analysis mechanism A and a control mechanism C.

The apparatus of FIG. 1 regulates the density of etching liquid via an injection pump $P_1$ metering hydrogen peroxide, an injection pump $P_2$ metering sulphuric acid, and an etching liquid circulation pump $P_3$. The discharge outlets of the injection pumps $P_1$ and $P_2$ communicate with an etching device (not shown in the Figs.). The discharge outlet of the circulating pump $P_3$ communicates with the etching device via a copper sulfate crystallizer (not shown in the Figs.) and a pipeline.

The sampling mechanism S has, as its main elements, a circulating pump 1 for the sample being analyzed, an overflow cell 2, and a sampling burette 3 which is a metering pump of the piston pump type, with a check valve. Solenoid valves $SV_4$ and $SV_5$ are provided at the input and output of the sampling burette 3. The circulating pump 1, the overflow cell 2 and a sample reservoir tank 4 constitute a sample circulating system. The sample such as, for example, etching liquid, is fed into the overflow cell 2 by the circulating pump 1, so that it is constantly refreshed in said cell. The etching solution under pressure of the circulating pump 1 enters the overflow cell 2 and returns to the sampling point. The reagent in the overflow cell 2 is sampled in fixed units and delivered to an analysis or analyzing cell 9.

The titration mechanism T has an alkali-reagent tank 5, a potassium permanganate reagent tank 6 and titration burettes 7 and 8 for titrating these reagents for the sample in the analysis cell 9. The titration burettes 7 and 8 have similar structures to that of the sampling burette 3.

The analysis mechanism A has a vessel, which is the analysis cell 9, for receiving the sample and reagents, a solenoid valve $SV_1$ supplying a cleansing liquid for cleansing the inner surfaces of the cell and a diluent for diluting the sample inside the cell and a level controller, or level switch, 10 controlling the cleansing liquid and the diluent so that they are supplied in prescribed quantities. The analysis mechanism A also has a pH-measuring electrode 11, an oxidation-reduction potential measuring electrode 12, an air pump 13 for agitating the liquid contents of the analysis cell 9, and a discharge pump 14 for discharging said liquid contents. The air pump 13 has a soda lime pipe 100 connected to its discharge outlet for removing carbon dioxide. A solenoid valve $SV_2$ is interposed between the analysis cell 9 and the discharge pump 14. A solenoid valve $SV_3$ is interposed between the air pump 13 and the analysis cell 9.

Figure 2:
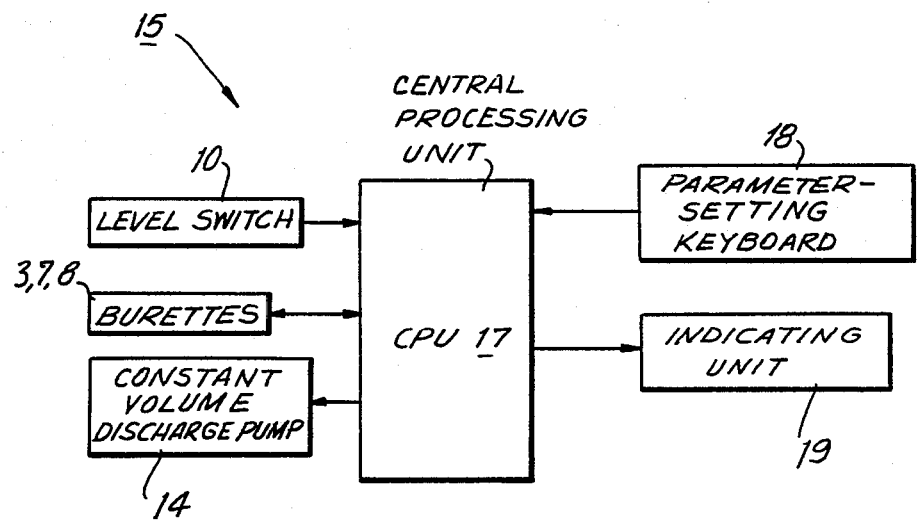
FIG. 2 is a simplified block diagram of an embodiment of the control unit 15 of the control mechanism C of FIG. 1.
Figure 3:
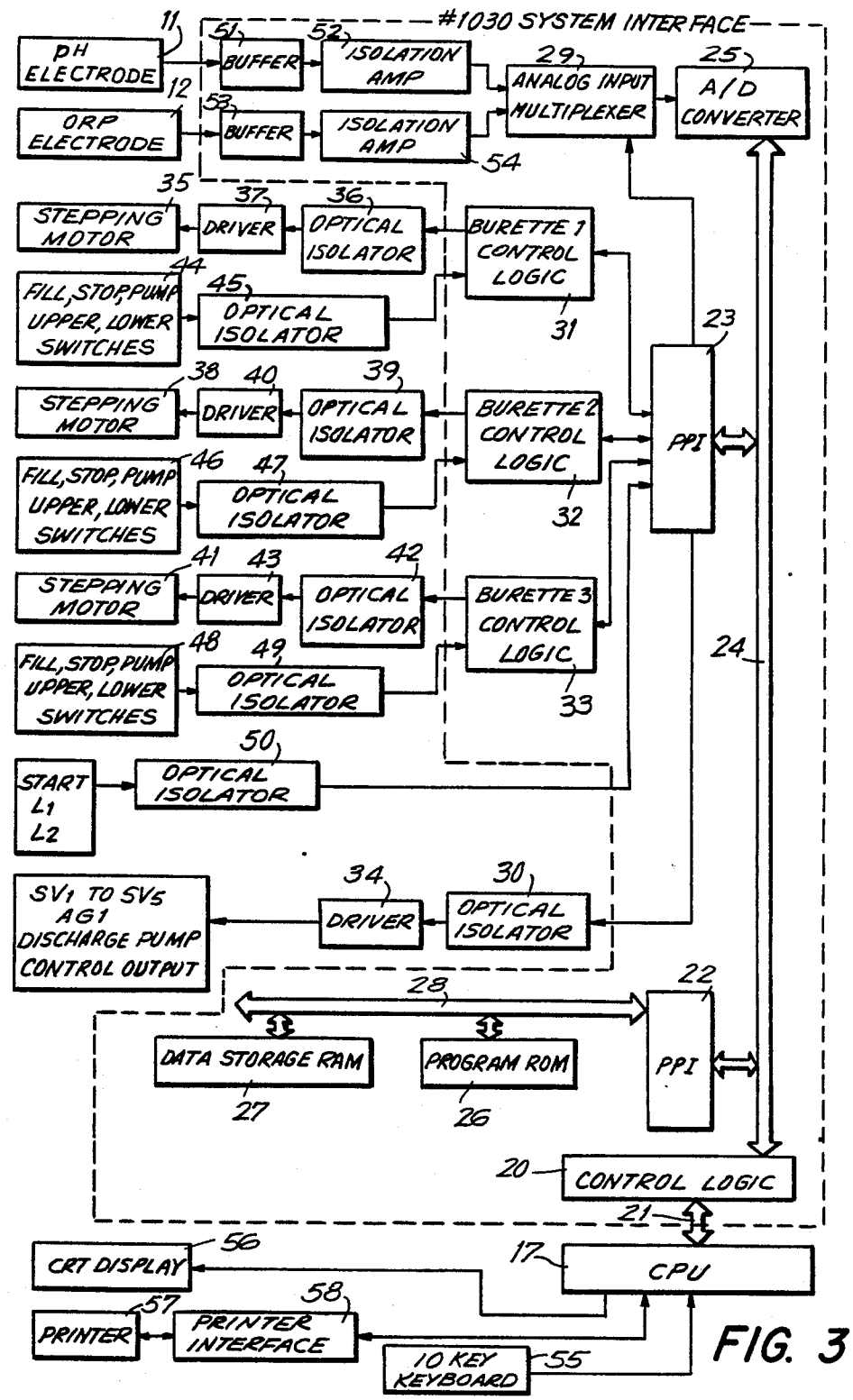
FIG. 3 is a more detailed diagram of the embodiment of FIG. 2.

The control mechanism C comprises a control unit 15 having a microcomputer, a display and a transducer, and a preferred embodiment of said control unit is shown in FIGS. 2 and 3.

As shown in FIG. 2, the control unit 15 comprises a central processing unit CPU 17 to which the level switch 10, the sampling burette 3, the titration burettes 7 and 8, the constant volume discharge pump 14, a parameter-setting keyboard 18 and an indicating unit 19 are connected.

FIG. 3 shows the control unit 15 in greater detail than FIG. 2. In FIG. 3, the central processing unit 17 is connected to control logic unit 20 via a bus 21 and said control logic unit is connected to plan position indicators or PPI 22 and 23 via a main bus 24, which is also connected to an analog to digital converter 25. The PPI 22 is connected to a program readout memory 26 and a data storage random access memory 27 via a bus 28.

The PPI 23 is connected to an analog input multiplexer 29, which is connected to the analog to digital converter 25, and to an optical isolator 30. The PPI 23 is also connected to a burette 1 control logic unit 31, a burette 2 control logic unit 32 and a burette 3 control logic unit 33, which may be the control logic units for the sampling burette 3, the titration burette 7 and the titration burette 8, respectively. The optical isolator 30 is connected to the solenoid valves $SV_1$ to $SV_5$, a unit $AG_1$, the discharge pump 14 and the control output via a driver 34. The burette 1 control logic unit 31 is connected to a first stepping motor 35 via an optical isolator 36 and a driver 37. The burette 2 control logic unit 32 is connected to a second stepping motor 38 via an optical isolator 39 and a driver 40. The burette 3 control logic unit 33 is connected to a third stepping motor 41 via an optical isolator 42 and a driver 43.

Fill, stop, pump, upper and lower switches 44, of the sampling burette 3, for example, are connected to the burette 1 control logic unit 31 via an optical isolator 45. Fill, stop, pump upper and lower switches 46, of the titration burette 7, for example, are connected to the burette 2 control logic unit 32 via an optical isolator 47. Fill, stop, pump, upper and lower switches 48, of the titration burette 8, for example, are connected to the burette control logic unit 33 via an optical isolator 49. A start unit, level 1 and level 2 indicators $L_1$ and $L_2$ are connected to the PPI 23 via an optical isolator 50. The pH electrode 11 is connected to the analog input multiplexer 29 via a buffer 51 and an isolation amplifier 52. The oxidation-reduction potential measuring electrode 12 is connected to the analog input multiplexer 29 via a buffer 53 and an isolation amplifier 54.

A 10 key keyboard 55 is connected to the central processing unit CPU 17. The CPU 17 is connected to a cathode ray tube display 56 and to a printer 57 via a printer interface 58. Each of the components and units of the control unit of FIG. 3 is of any suitable known type for performing the function ascribed to it. The components 20, 22, 23, 24, 25, 26, 27, 28, 29, 31, 32, 33, 51, 52, 53 and 54 are included in a No. 1030 system interface.

The control unit 15 fulfills the following functions.

a. Operate the solenoid valves $SV_1$ to $SV_5$, the sampling burette 3, the titration burettes 7 and 8, the air pump 13 and the discharge pump 14 in the prescribed sequence at the prescribed timing.

b. Open and close the solenoid valve $SV_1$ when signals from the level switch 10 are received.

c. Stop the operations of the titration burettes 7 and 8 when signals from the pH-measuring electrode 11 and the oxidation-reduction potential measuring electrode 12 are received when a prescribed pH or potential is reached, while detecting the end point of the titration and reading the titer of the reagents at said end point from said titration burettes.

d. Compute the density of the hydrogen peroxide or sulfuric acid in the sample from the quantity read, convert the difference between a predetermined or preset density and the density thus obtained into a period of time when the measured density is lower than the predetermined density, and operate the injection pump $P_1$ or $P_2$ for that period of time.

e. Operate the circulating pump $P_3$ when the density of copper in the sample determined in the same manner is higher than a predetermined or preset density, so that the excess copper is transferred to the crystallizer to separate and collect copper sulfate while returning the separated liquid to the etching device.

f. Display and record the measured densities of the hydrogen peroxide, sulfuric acid and copper, while producing an alarm when these densities have abnormal values, etc.

Piping 16 supplies cleansing water and diluent water.

The automatic titration analysis controlling apparatus of the invention, constituted as hereinbefore described, performs a course of analyzing operations and an operation of regulating the density of the etching liquid in accordance with the following sequence based on the output from the control mechanism C.

I. Analyzing operation (1) Preparation of sample (i) Washing analysis cell 9 with a sample itself.

The solenoid valves $SV_4$ and $SV_5$ are opened and the sampling burette 3 is operated, so that a prescribed quantity of sample or reagent is injected into the analysis cell 9. The solenoid valve $SV_3$ is then opened, and the air pump 13 is operated, so that the sample is agitated by air for a prescribed period of time. The solenoid valve $SV_2$ is opened and the discharge pump 14 is operated for a prescribed period of time, so that the sample is discharged. The foregoing operations are repeated a predetermined or preset number of times.

(ii) Washing of analysis cell 9 with water.

The solenoid valve $SV_1$ is opened and tap water 16 is injected up to a cleansing level $L_1$. After the water is raised to the cleansing level inside the analysis cell 9 by the opening of the solenoid valve $SV_1$, the solenoid valve $SV_3$ is opened and the air pump 13 is operated, so that the agitator starts to operate and the tap water is agitated for a prescribed time. The tap water is then discharged in the same manner as in (i). These operations are repeated a predetermined number of times.

(iii) Injection of diluent water and sample into analysis cell 9.

Tap water is injected up to a dilution level $L_2$ in the same manner as in (ii) and a prescribed quantity of sample is thereafter injected in the same manner as in (i). The dilution and the agitation and mixing of the sample by the air pump 13 are performed for a prescribed time.

(2) Titration analysis (i) Titration of density of sulfuric acid using NaOH or $Na_2CO_3$ as the reagent.

(ii) Titration of density of total quantity of copper.

This is performed in the same manner as in (1)(i). The analysis of the acidity and total quantity of copper may be performed in one titration when a sampling point is identical, as it is in this example. After the completion of the titration of the acidity or the total quantity of copper, the discharge pump 14 is operated for a prescribed period of time to discharge the liquid contents of the analysis cell 9.

(iii) Titration of density of hydrogen peroxide solution.

The analysis cell 9 is first washed with a sample itself in the same manner as in (1)(i) and then a sample and diluent is injected into said analysis cell by the methods described in (1)(ii) and (1)(iii). Titration is performed, using $KMnO_4$ as the reagent. After the completion of the titration, the discharge pump 14 is operated for a prescribed period of time to discharge the liquid contents of the analyzing cell 9.

II. Adjustment of density of etching liquid, display of density of sample, etc.

(1) The titer of the reagent used for the analysis is read at the end point of the titration, and the density of the sample, such as, for example, the density of the sulfuric acid, is computed.

(2) When the density of hydrogen peroxide or sulfuric acid thus obtained is lower than a predetermined or preset density, the difference between said preset density and the measured density is converted into a period of time. The injection pump $P_1$ or $P_2$ is operated for that period of time to supplement the sulfuric acid or hydrogen peroxide solution. In addition, the measured density, etc., are displayed.

A supplementary explanation of the relationship of the pH-measuring electrode 11, the oxidation-reduction potential measuring electrode 12, the control mechanism C and the titration burettes 7 and 8 is as follows. While changes in the physical properties of a sample caused by the titration operation are being delivered continuously to the control mechanism C by each of these electrodes, said control mechanism detects the speed or rate of said changes in the physical properties in relation to the titer of the reagent, as well as the end point of the titration based thereon. The control mechanism C conducts an operation of memorization of the end point of the titration and adjusts the speed or rate of titration of the reagent to be smaller or larger according to the magnitude of the changes in the physical properties. Furthermore, when a predetermined or preset pH or oxidation-reduction potential is reached, it stops the operations of the titration burettes 7 and 8.

While the aforedescribed operations are being conducted repeatedly, the circulating pump $P_3$ continues its operation until an output indicating that the density of copper is lower than the preset density is delivered, based on the subsequent titration analysis. Thus, the circulating pump $P_3$ operates in such a manner that it turns on when the measured density is greater than the preset density and turns off when the measured density is less than, or equal to, said preset density.

The automatic titration analysis apparatus of the embodiment of FIG. 1 is also provided with a mechanism for regulating the density of the etching liquid. However, this mechanism may be omitted.

It is possible to modify the embodiment of FIG. 1 so that the overflow liquid from the sample reservoir tank 4 flows into the overflow cell 2. An agitator with agitating blades may be utilized instead of the air pump 13. The discharge pump 14 may be omitted by a design in which the liquid contents of the analyzing cell 9 are discharged under their own weight. The analysis cell 9 may be cleansed or the liquid contents thereof may be agitated by the discharge outlet of the discharge pump 14 opening into said analysis cell. Pipes may be provided for supplying cleansing liquid to communicate with the sampling burette 3 and the titration burettes 7 and 8 for cleansing the parts thereof in contact with liquid. A plurality of sampling, titration and analysis mechanisms S, T and A may be arranged in parallel so that an analysis operation may be conducted constantly in any of the analysis cells. When the sample liquid is of a high viscosity, it is recommended that a gear pump be utilized instead of the sampling burette 3.

The discharge outlet of the air pump 13 is connected to a soda lime pipe 100 for removing carbon dioxide. This is for the purpose of turning air into a gas which is chemically inert with respect to the liquid contents of the analysis cell 9. Accordingly, it is obvious that an inert gas such as $N_2$ may be utilized instead of air with carbon dioxide removed. The liquid contents may also be agitated by air supplied directly, dependent upon the type of liquid.

In measuring the concentration of $H_2O_2$, an acid-reducing potential electrode is used as the electrode and $\frac{1}{8}$ $N$-$KMnO_4$ is used as the titration reagent. The titration burette is operated and titration proceeds to the voltage which is memorized by the microcomputer. The concentration of the $H_2O_2$ is then measured.

In measuring the concentration of $H_2SO_4$, a glass electrode is used as the electrode and 2 N-NaOH is used as the titration reagent. The titration burette is operated, titration proceeds to the pH which is memorized by the microcomputer and the concentration of the $H_2SO_4$ is measured by the titration volume flowing to the end point.

In measuring the concentration of Cu, a glass electrode is used as the electrode and 2 N-NaOH is used as the titration reagent. The titration burette starts to operate and titration proceeds to the preset pH value. The copper concentration is measured by the titration volume flowing to the end point. $H_2SO_4$ and Cu may be measured by a single titration.

When the measured concentration is lower than the preset magnitude, the difference between the preset and measured concentrations is converted to time. For such a period of time, a supplement is obtained by operation of the constant discharge pump 14. The discharge pump 14 operates for a fixed period of time, so that the reagent may be exhausted.

The apparatus of the invention permits an almost-unattended, rapid, repeated and continuous attainment of accurately measured values. Furthermore, because of the built-in feedback control mechanism of the illustrated embodiment, the apparatus has the advantage that the control of a process such as, for example, an etching process, and the qualities in a sample generating source may be greatly rationalized. This results in the attainment of a large energy-saving, a simplification of the maintenance and controls of the apparatus of the sample generating source and an improvement and stabilization of the quality of products, etc.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Automatic titration analysis apparatus, comprising:

a sampling mechanism for capturing a predescribed quantity of a sample for analysis in accordance with a first signal and dispensing said sample, said sample having a density, said sampling mechanism including a sample supply container, a pipe line, a circulating pump for recirculating said sample within said pipeline, an overflow cell connected to both a discharge outlet of said circulating pump and an inlet of said sample supply container through said pipe line, and a metering pump drawing a predescribed quantity of said sample from said overflow cell and dispensing said sample to an analysis vessel;

a titration mechanism for titrating a predescribed quantity of one of two reagents for analysis of said sample and providing a titer according to second signals, said titration mechanism including two reservoir tanks and two respective titration burettes for said two reagents, one of said reagents being sodium hydroxide or sodium carbonate and the other of said reagents being potassium permanganate;

an analysis mechanism for receiving said sample dispensed by said sampling mechanism, analyzing said thus-dispensed sample, and converting a change in the physical properties of said sample caused by titration into an electrical quantity, said analysis mechanism including a vessel receiving said sample from said sampling mechanism and said reagents from said titration mechanism;

a mechanism for supplying a diluent to dilute said sample which comprises a diluent feed pipe a valve disposed therein, a level-controlling switch for controlling liquid level within said vessel between two predetermined levels and for controlling the diluent so that it is supplied in predescribed quantities, an electrode situated in said vessel for measuring pH of said sample and thereby measuring concentration of $H_2SO_4$ or Cu in said sample when titrated with the sodium carbonate or sodium hydroxide reagent, an electrode situated in said vessel for measuring oxidation-reduction of said sample and thereby measuring concentration of $H_2O_2$ in said sample when titrated with the potassium permanganate reagent, and mechanism for agitating and discharging liquid in said vessel, comprising a gas pump communicating with said vessel for supplying a gas thereinto, and a constant volume discharge pump for discharging the liquid from the vessel; and a control mechanism including analog-to-digital converter means for providing and applying said first signal to said sampling mechanism and providing and applying said second signals to said titration mechanism, receiving said titer provided by said analysis mechanism, setting the quantity of said sample converted and titer of said reagents to prescribed values in accordance with said electrical quantity converted by said analysis mechanism, reading said titer at an end point of said titration, outputting density of said sample calculated therefrom, and controlling in sequence operations of said sampling, titration, and analysis mechanisms in the sequence of sampling, titration, analysis and calculation and output of said measured density, wherein said control mechanism comprises a central processing unit coupled to said level switch, said titration burettes, and said discharge pump, a parameter-setting keyboard coupled to said central processing unit, an indicating unit coupled to said central processing unit for indicating the measured density of $H_2O_2$, $H_2SO_4$ and Cu, a control logic unit through which said centnral processing unit is coupled to said analog-to-digital convertor means, an analog input multiplexer coupled to said analog-to-digital converter means, a buffer and isolation amplifier through which said pH electrode is coupled to said multiplexer, a buffer and isolation amplifier through which said oxidation-reduction electrode is coupled to said multiplexer, two plan position indicators connected to said control logic unit and to said analog-to-digital converter means through a main bus, a program readout memory and a data storage random access memory connected to a first one of said plan position indicators, said second one of said plan position indicators being coupled to said multiplexer, an optical isolator and a drive through which said second plan position indicator and said discharge pump, said level switch, said diluent supply mechanism, said gas pump, and said sampling mechanism are coupled to second plan position indicator, a start unit and level indicators, and an optical isolator through which the same are coupled to said second plan position indicator, three burette control logic units, each coupled to said second plan position indicator, a first pair of optical isolators coupled to a first one of said burette control logic units, fill, stop, pump, upper and lower switches of said metering pump coupled to a first one of said first pair of optical isolators, a first stepping motor and a drive through which said first stepping motor is coupled to a second one of said first pair of optical isolators, a second pair of optical isolators coupled to a second one of said burette control logic units, fill, stop, pump, upper and lower switches of one of said two titration burettes coupled to a first one of said second pair of optical isolators, a second stepping motor a drive through which said second stepping motor is coupled to a second one of said second pair of optical isolators, a third pair of optical isolators coupled to a third one of said burette control logic units, fill, stop, pump, upper and lower switches of the other of said two titration burettes coupled to a first one of said third pair of optical isolators, and a third stepping motor and a driver through which said third stepping motor is coupled to a second one of said third pair of optical isolators.

2. The apparatus of claim 1, wherein said indicating unit comprises a cathode ray tube display coupled to said central processing unit, and a printer and a printer interface through which said printer is coupled to said central processing unit.

3. The apparatus of claim 1, wherein said control mechanism constitutes means for setting the value of said titer of said reagents in accordance with said electrical quantity provided by said analysis mechanism.

4. The apparatus of claim 1, wherein said metering pump for collecting said samples is a piston pump provided with a check valve.

5. The apparatus of claim 1, wherein said agitating and discharging mechanism additionally comprises a solenoid valve through which said gas pump communicates with said vessel, and a solenoid valve through which said discharge pump communicates with said vessel.

6. The apparatus of claim 1, wherein each said titration burette is a piston pump provided with a check valve.

7. The apparatus of claim 1, wherein said gas pump additionally comprises means for removing carbon dioxide from gas therein at a discharge outlet thereof.

8. The apparatus of claim 1, wherein said indicating unit additonally comprises alarm means for generating an alarm when results of the analysis meet predetermined criteria.

9. The apparatus of claim 1, wherein said sampling mechanism additionally comprises a pair of solenoid valves, with said overflow cell and said metering pump communicating through a first one of said pair of solenoid valves, and said metering pump communicating with said vessel of said analyzing mechanism through a second one of said pair of solenoid valves.

10. The apparatus of claim 1, wherein said metering pump is a sampling burette provided with a check valve.

* * * * *